United States Patent [19]
Lunde

[11] Patent Number: 5,948,732
[45] Date of Patent: Sep. 7, 1999

[54] HERBICIDAL AGENT BASED ON DEET AND METHOD OF USING SAME

[76] Inventor: Nordan J. Lunde, P.O. Box 83, Davenport, N. Dak. 58021

[21] Appl. No.: 09/007,481

[22] Filed: Jan. 15, 1998

[51] Int. Cl.⁶ ................................................. A01N 37/18
[52] U.S. Cl. ........................................... 504/337; 514/617
[58] Field of Search ............................. 504/337; 514/617

[56] References Cited

U.S. PATENT DOCUMENTS 2,408,389  10/1946  Gertler ........................................ 167/30
5,695,773  12/1997  Schapira et al. ........................ 424/405

*Primary Examiner*—S. Mark Clardy

[57] ABSTRACT

A herbicidal agent based on DEET (N,N-diethyl-m-toluamide) and method of using same for killing and controlling undesirable plant growth, such as leafy spurge, without significantly affecting desirable plant growth such as trees and grasses. The composition contains a carrier fluid and DEET. The preferred concentration of DEET is in the range of from about 10% to 35% by weight of the composition. The composition can be successfully applied to various families of weeds to kill and control their growth.

10 Claims, No Drawings

HERBICIDAL AGENT BASED ON DEET AND METHOD OF USING SAME

BACKGROUND OF THE INVENTION

1. Field of the Invention

The present invention relates generally to herbicidal agents and more specifically it relates to a herbicidal agent based on DEET (N,N-diethyl-m-toluamide) for killing and controlling undesirable plant growth without damaging desirable plant growth such as grasses, shrubs and trees. The present invention particularly relates to the killing and controlling of leafy spurge.

Conventional herbicides, such as Tordon or 2-4-D, are effective in killing and controlling undesirable plant growth such as leafy spurge, however, conventional herbicides are also kill desirable plant growth. With conventional herbicides, great care must be executed by the spray operator to prevent tree rows, crops, shrubs and grasses from becoming in contact with the conventional herbicides. The operator must always compensate for the direction and strength of the wind. If the conventional herbicides come in contact with the desirable plants, often the desirable plants will be severely damaged or completely killed.

When spraying for undesirable plant growth, such as leafy spurge, the undesirable plant growth is within trees and shrubs, or near water. Convention herbicides will kill or severely damage the desirable plant growth. Also, conventional herbicides usually cannot be applied to environmentally sensitive areas, such as near water, where herbicide use is restricted. Hence, there is a need for a herbicide which can be applied to undesirable plant growth without severely damaging desirable plant growth.

2. Description of the Prior Art

Formulations containing DEET have been previously described by other patents. For example, U.S. Pat. No. 4,272,282 to Hansen et al, U.S. Pat. No. 5,575,988 to Knowles, Jr. et al; U.S. Pat. No. 5,610,194 to Polefka et al; U.S. Pat. No. 4,612,327 to Matukuma et al; U.S. Pat. No. 4,956,129 to Scher et al; U.S. Pat. No. 5,466,460 to McMahon et al; U.S. Pat. No. 5,332,584 to Scher et al; U.S. Pat. No. 5,292,533 to McMahon et al; U.S. Pat. No. 5,160,529 to Scher et al; U.S. Pat. No. 5,120,542 to Scher et al; U.S. Pat. No. 5,621,013 to Beldock et al; U.S. Pat. No. 4,157,983 to Golden; U.S. Pat. No. 4,933,167 to Scher et al; U.S. Pat. No. 5,221,535 to Domball are illustrative of such prior art.

Hansen et al (U.S. Pat. No. 4,272,282) discloses a herbicidal mixture containing a herbicidal substituted anilide and substituted dichloroacetamide as antidote therefor. Hansen et al does not disclose the use of DEET for controlling various types of undesirable plants.

Knowles, Jr. et al (U.S. Pat. No. 5,575,988) discloses a combination sunscreen and insect repellent comprised of an inorganic micronized inorganic substance and DEET. However, Knowles does not disclose the use of DEET for controlling various types of undesirable plants.

Polefka et al (U.S. Pat. No. 5,610,194) discloses an insect repellent comprising an amount of DEET and an amount of N-methyl neodecanamide (MNDA) However, Polefka does not disclose the use of DEET for controlling various types of undesirable plants.

While conventional herbicides may be suitable for the particular purpose to which they address, they are not as suitable for killing and controlling undesirable plant growth without damaging desirable plant growth such as grasses, shrubs and trees. Conventional herbicides severely damage or kill desirable plant growth when placed in contact. Also, conventional herbicides severely damage or kill crops when sprayed near a cultivated field.

In these respects, the herbicidal agent based on DEET according to the present invention substantially departs from the conventional methods of use and compositions of the prior art, and in so doing provides a composition and a method of using the composition primarily developed for the purpose of killing and controlling undesirable plant growth without damaging desirable plant growth such as grasses, shrubs and trees.

SUMMARY OF THE INVENTION

A primary object of the present invention is to provide a herbicidal agent based on DEET and a method of using the same that will overcome the shortcomings of the prior art.

Another object is to provide a herbicidal agent based on DEET and a method of using the same that kills and controls undesirable plant growth such as leafy spurge, dandy lions, milkweed, spotted napweed, Canadian thistle and various other weeds.

An additional object is to provide a herbicidal agent based on DEET and a method of using the same that does not severely damage desirable plant growth such as grasses, shrubs, trees, conventional crops and various other desirable plants.

A further object is to provide a herbicidal agent based on DEET and a method of using the same that has an application cost approximately the same as conventional herbicides.

Another object is to provide a herbicidal agent based on DEET and a method of using the same that does not harm the environment such as environmentally sensitive wetlands.

Another object is to provide a herbicidal agent based on DEET and a method of using the same that is relatively safe for humans and livestock to come in contact with.

Further objects of the invention will appear as the description proceeds.

DESCRIPTION OF THE PREFERRED EMBODIMENT

DEET (N,N-diethyl-m-toluamide) is readily commercially available, for example, from Morflex Chemical, Inc. The amount of DEET which may be included in the compositions of the invention is from about 5% by weight to about 95% by weight. Preferably, the amount of DEET will be in the range of from about 10% by weight to about 35% by weight. A concentration of from about 20% by weight to about 30% by weight is most preferred. Applications of the herbicide may be accomplished by aerial or ground spraying utilizing conventional spray equipment.

DEET is most commonly utilized in household products such as insect repellents (an example is Deep Woods Off brand insect repellent). Since DEET is directly applied to human skin, extensive research has been conducted on the health affects of DEET. DEET has been noted to cause only moderate irritation of the eyes. DEET has little reaction with the skin of humans, other than mucous membranes and abraded skin. As with most chemicals, ingestion and inhalation may result in serious health affects if in high dosages. Also, none of the components in DEET is a known carcinogen.

The herbicide composition preferably comprises an amount of DEET and an amount of water mixed together. The amount of DEET is preferably from 10% by weight to about 35% by weight for maximum effectiveness when applied to the undesirable plant growth. In addition, an amount of oil is preferably combined with the DEET-water composition to increase the amount of DEET contacting the surface of the undesirable plants and remaining there without dripping off.

In use, an amount of DEET is combined with a fluid such as water to form the herbicide composition. Preferably, the amount of DEET is combined with an oil-in-water emulsion, or a water-in-oil emulsion for improving application to the undesirable plants. The herbicide composition containing DEET is thereafter directly applied to the undesirable plant growth, even if near desirable plant growth. After approximately one day, a noticeable difference in the structure of the undesirable plants occurs, with little noticeable difference in the structure of the desirable plants. After seven days, the leaves, flowers and the main stem of the undesirable plants are dying. After 30 days, kill rates of up to 95% can be achieved with a mixture of approximately 25% DEET by weight.

The present composition and method of using same provides an effective herbicide for undesirable plant growth while not severely harming desirable plant growth. The resulting material is stable over time and relatively harmless to humans and animals.

The invention further is illustrated by the following examples, which are not intended to be limiting in any way. The measurements for the following examples were conducted utilizing conventional measuring methods common in the industry to ensure accuracy.

EXAMPLE #1

A herbicide composition comprising approximately 28% DEET by weight was applied to leafy spurge during the early stage of its growth. The weather conditions and the leafy spurge kill rates are as follow:

| Weather Conditions | | Percentage Leafy Spurge Killed | | | | Percentage Re-Growth Rate | | | Percentage of Affects On Desirable Plants | | | |
|---|---|---|---|---|---|---|---|---|---|---|---|---|
| Temp. (F.) | Sky | 24 HRs | 5 Days | 10 Days | 30 Days | 5 Days | 20 Days | 30 Days | Grasses | Shrubs | Trees | Crops |
| 65 | PC | 12% | 55% | 73% | 79% | 0% | 10% | 25% | <10% | <5% | N.A. | N.A. |
| 63 | PS | 15% | 65% | 79% | 88% | 0% | 15% | 20% | <10% | N.A. | N.A. | N.A. |
| 65 | PS | 12% | 67% | 76% | 90% | 0% | 10% | 22% | <10% | N.A. | N.A. | N.A. |
| 74 | OC | * | 45% | 78% | 58% | 0% | 5% | 11% | <5% | N.A. | N.A. | N.A. |
| 72 | OC | * | 52% | 80% | 86% | 0% | 0% | 10% | <7% | N.A. | N.A. | N.A. |

PC* - Partly Cloudy;
PS - Partly Sunny;
OC - Overcast;
S - Sunny
*½ inch of rain was received immediately after applying the herbicide.

EXAMPLE #2

A herbicide composition comprising approximately 6% DEET by weight was applied to leafy spurge during the early stage of its growth. The weather conditions and the leafy spurge kill rates are as follow:

| Weather Conditions | | Percentage Leafy Spurge Killed | | | | Percentage Re-Growth Rate | | | Percentage of Affects On Desirable Plants | | | |
|---|---|---|---|---|---|---|---|---|---|---|---|---|
| Temp. (F.) | Sky | 24 HRs | 5 Days | 10 Days | 30 Days | 5 Days | 20 Days | 30 Days | Grasses | Shrubs | Trees | Crops |
| 78 | S | 2% | 5% | 10% | 30% | 0% | 23% | 62% | 0% | 0% | 0% | N.A. |
| 79 | S | 3% | 6% | 12% | 31% | 0% | 21% | 60% | 0% | 0% | 0% | N.A. |

PC - Partly Cloudy;
PS - Partly Sunny;
OC - Overcast;
S - Sunny

EXAMPLE #3

A herbicide composition comprising approximately 12% DEET by weight was applied to leafy spurge during the middle stage of its growth. The weather conditions and the leafy spurge kill rates are as follow:

| Weather Conditions | | Percentage Leafy Spurge Killed | | | | Percentage Re-Growth Rate | | | Percentage of Affects On Desirable Plants | | | |
|---|---|---|---|---|---|---|---|---|---|---|---|---|
| Temp. (F.) | Sky | 24 HRs | 5 Days | 10 Days | 30 Days | 5 Days | 20 Days | 30 Days | Grasses | Shrubs | Trees | Crops |
| 76 | S | 7% | 13% | 20% | 27% | 0% | 15% | 42% | 0% | 0% | 0% | N.A. |
| 80 | S | 10% | 15% | 19% | 30% | 0% | 14% | 39% | 0% | 0% | 0% | N.A. |

PC - Partly Cloudy;
PS - Partly Sunny;
OC - Overcast;
S - Sunny

EXAMPLE #4

A herbicide composition comprising approximately 14% DEET by weight was applied to leafy spurge during the middle stage of its growth. The weather conditions and the leaf spurge kill rates are as follow:

| Weather Conditions | | Percentage Leafy Spurge Killed | | | | Percentage Re-Growth Rate | | | Percentage of Affects On Desirable Plants | | | |
|---|---|---|---|---|---|---|---|---|---|---|---|---|
| Temp. (F.) | Sky | 24 HRs | 5 Days | 10 Days | 30 Days | 5 Days | 20 Days | 30 Days | Grasses | Shrubs | Trees | Crops |
| 84 | S | 12% | 18% | 29% | 44% | 0% | 6% | 31% | 4% | 4% | 9% | N.A. |
| 84 | S | 10% | 20% | 31% | 47% | 0% | 5% | 30% | 4% | 6% | 9% | N.A. |

PC - Partly Cloudy;
PS - Partly Sunny;
OC - Overcast;
S - Sunny

EXAMPLE #5

A herbicide composition comprising approximately 17% DEET by weight was applied to leafy spurge during the late stage of its growth. The amount of DEET was combined with a water-in-oil emulsion. The weather conditions and the leafy spurge kill rates are as follow:

| Weather Conditions | | Percentage Leafy Spurge Killed | | | | Percentage Re-Growth Rate | | | Percentage of Affects On Desirable Plants | | | |
|---|---|---|---|---|---|---|---|---|---|---|---|---|
| Temp. (F.) | Sky | 24 HRs | 5 Days | 10 Days | 30 Days | 5 Days | 20 Days | 30 Days | Grasses | Shrubs | Trees | Crops |
| 82 | PS | 10% | 18% | 28% | 47% | 0% | 7% | 26% | 4% | 10% | 10% | N.A. |
| 82 | PS | 8% | 21% | 31% | 48% | 0% | 5% | 23% | 4% | 8% | 10% | N.A. |

PC - Partly Cloudy;
PS - Partly Sunny;
OC - Overcast;
S - Sunny

EXAMPLE #6

A herbicide composition comprising approximately 30% DEET by weight was applied to leafy spurge during the late stage of its growth. The amount of DEET was combined with a water-in-oil emulsion. The weather conditions and the leafy spurge kill rates are as follow:

| Weather Conditions | | Percentage Leafy Spurge Killed | | | | Percentage Re-Growth Rate | | | Percentage of Affects On Desirable Plants | | | |
|---|---|---|---|---|---|---|---|---|---|---|---|---|
| Temp. (F.) | Sky | 24 HRs | 5 Days | 10 Days | 30 Days | 5 Days | 20 Days | 30 Days | Grasses | Shrubs | Trees | Crops |
| 77 | S | 10% | 30% | 57% | 90% | 0% | 2% | 10% | 4% | 10% | 10% | N.A. |
| 78 | S | 12% | 32% | 61% | 92% | 0% | 1% | 9% | 4% | 12% | 12% | N.A. |
| 74 | S | 10% | 34% | 66% | 91% | 0% | 2% | 9% | 5% | 8% | 6% | N.A. |
| 75 | S | 8% | 29% | 62% | 87% | 0% | 1% | 9% | 4% | 10% | 5% | N.A. |

PC - Partly Cloudy;
PS - Partly Sunny;
OC - Overcast;
S - Sunny

It should be noted that the percentage of desirable plant growth affected represents only plants which received discoloration or the end of the leaves were burnt off. None of the desirable plants were pruned or killed as a result of the application of the herbicide thereto. The desirable plants fully recovered within a relatively short period of time. It should also be noted that the herbicide killed and controlled the undesirable plants in the vicinity of the leafy spurge.

Observing the applications of the herbicide in the early and late stages of growth of leafy spurge disclosed some interesting information. When the herbicide was applied during the late stages of growth, the re-growth rate was less than 50% than when applied during the early stages of growth. Even though it is expected that early stage re-growth will be higher than the late stage re-growth, the substantial difference between the two applications was never expected when compared to conventional herbicides.

As to a further discussion of the manner of usage and composition of the present invention, the same should be apparent from the above description. Accordingly, no further discussion relating to the manner of usage will be provided.

With respect to the above description then, it is to be realized that the optimum relationships for the components of the invention, to include variations in proportions and manner of use are deemed readily apparent and obvious to one skilled in the art.

Therefore, the foregoing is considered as illustrative only of the principles of the invention. Further, since numerous modifications and changes will readily occur to those skilled in the art, it is not desired to limit the invention to the exact composition and use shown and described, and accordingly, all suitable modifications and equivalents may be resorted to, falling within the scope of the invention.

I claim:

1. A method of utilizing a herbicide to control undesirable plant growth without damaging desirable plant growth, comprising the steps of:

(a) providing a herbicide comprised of N,N-diethyl-m-toluamide; and (b) applying said amount of N,N-diethyl-m-toluamide to undesirable plants.

2. The method of claim 1, wherein said herbicide includes an amount of water.

3. The method of claim 2, wherein the concentration of said amount of N,N-diethyl-m-toluamide is in the range of from about 5% to 95% by weight of the composition.

4. The method of claim 3, wherein said herbicide includes an amount of oil.

5. The method of claim 4, wherein said step of applying said herbicide composition occurs in the late stage of the growing season prior to or slightly after the first freeze.

6. The method of claim 5, wherein said step of applying said herbicide composition occurs in the early stage of plant growth.

7. A method of utilizing a herbicide to control undesirable plant growth without damaging desirable plant growth, comprising the steps of:

(a) providing an amount of N,N-diethyl-m-toluamide; and (b) applying said amount of N,N-diethyl-m-toluamide to undesirable plants.

8. The method of claim 7 including an amount of water.

9. The method of claim 8, wherein the concentration of said amount of N,N-diethyl-m-toluamide is in the range of from about 5% to 95% by weight of the composition.

10. The method of claim 9 including an amount of oil.

* * * * *